United States Patent [19]

Young et al.

[11] 4,149,938

[45] Apr. 17, 1979

[54] ELECTROCHEMICAL DETECTION DEVICE

[75] Inventors: Richard N. Young, San Jose, Calif.; Judd R. Wilkins, Hampton, Va.

[73] Assignee: The United States of America as represented by the Administrator of the National Aeronautics and Space Administration, Washington, D.C.

[21] Appl. No.: 856,460

[22] Filed: Nov. 30, 1977

[51] Int. Cl.² .............................................. C12K 1/04
[52] U.S. Cl. .................................. 195/127; 204/195 B
[58] Field of Search ...................... 195/127; 204/195 B

[56] References Cited
U.S. PATENT DOCUMENTS

| | | | |
|---|---|---|---|
| 3,162,585 | 12/1964 | De Ford et al. | 204/195 B X |
| 3,520,660 | 7/1970 | Webb | 195/127 X |
| 3,633,012 | 1/1972 | Wilhelmson | 195/127 X |
| 3,694,317 | 9/1972 | Scher | 195/127 X |
| 4,009,078 | 2/1977 | Wilkins et al. | 195/127 X |

Primary Examiner—Raymond N. Jones
Assistant Examiner—Robert J. Warden
Attorney, Agent, or Firm—William H. King; John R. Manning; Howard J. Osborn

[57] ABSTRACT

An electrochemical detection device for detecting micro-organisms. A standard pH reference electrode and a platinum cathodic electrode are positioned in a container with suitable nutrient medium for microbial growth plus the sample to be tested. The two electrodes are connected to electronic circuitry including an up-/down counter which counts up for the first 80 minutes after a test has been initiated. Then the potential between the two electrodes is tracked by the electronic circuitry and after there is a change of 10 mv a signal is sent to the up/down counter to cause it to reverse its count. Thereafter when there is a additional 20 mv change in the potential between the two electrodes another signal is sent to the up/down counter signalling it to stop. The resulting count on the counter is equal to the length of time for the inoculum to begin the production of measurable amounts of $H_2$ after inoculation. This length of time is indicative of a endpoint.

9 Claims, 1 Drawing Figure

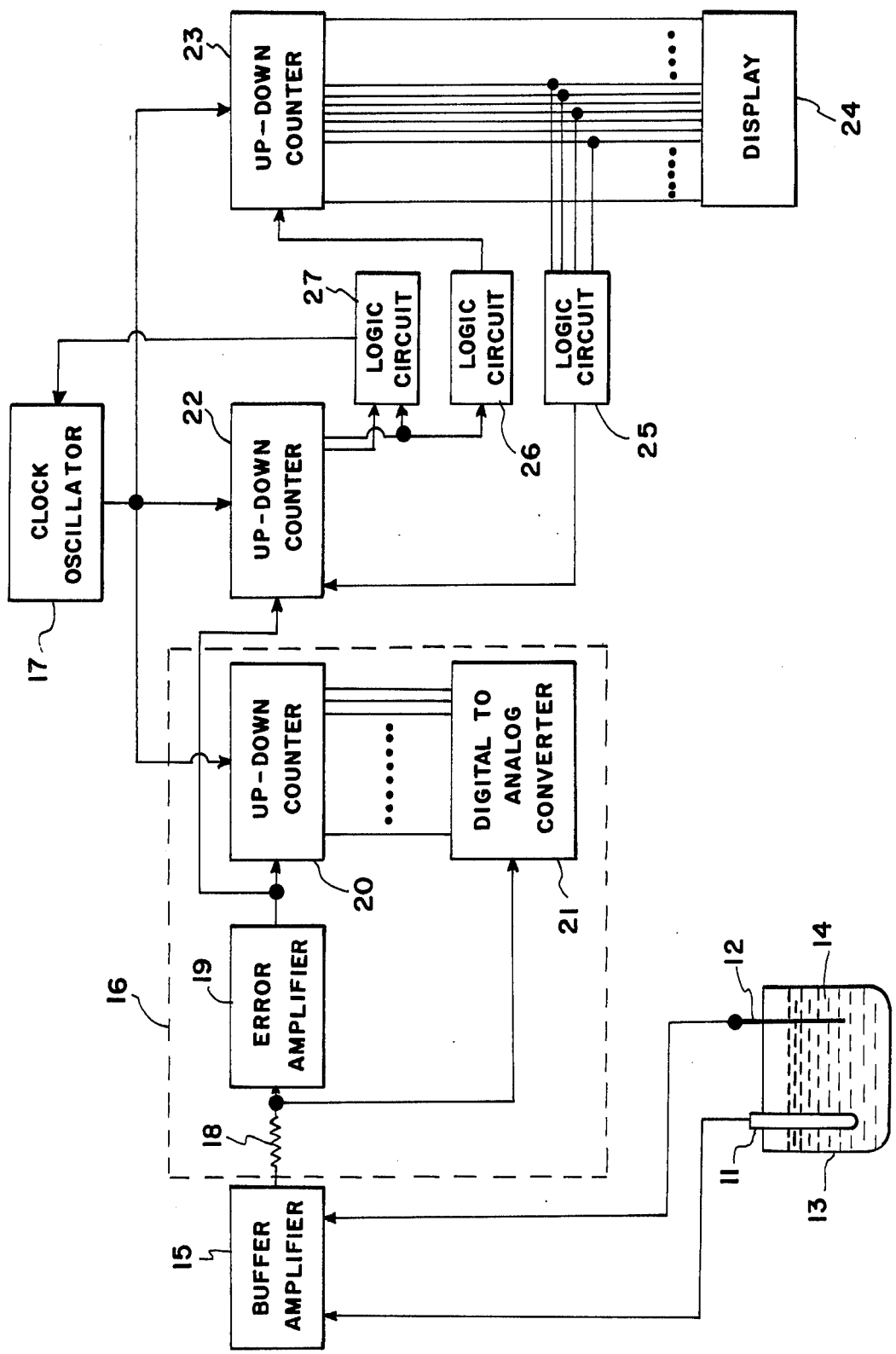

ELECTROCHEMICAL DETECTION DEVICE

ORIGIN OF THE INVENTION

The invention described herein was made by employees of the U.S. Government and may be manufactured and used by or for the government for governmental purposes without the payment of any royalties thereon or therefor.

BACKGROUND OF THE INVENTION

This invention relates generally to electrochemical detection of micro-organisms and more specifically concerns a device for detecting micro-organisms by measuring the elapsed time between inoculation and the initial increase in potential due to $H_2$ evolution.

An electrochemical method for detecting micro-organisms based on a linear relationship between initial cell concentration and the time molecular hydrogen ($H_2$) is detected is disclosed in U.S. Pat. No. 4,009,078 which was issued on Feb. 22, 1977. The apparatus used by that method was a reference electrode and a platinum electrode connected to a strip chart recorder. An endpoint was recorded as the elapsed time between inoculation and the initial increase in potential due to $H_2$ evolution and was read directly from the strip chart recording. The inherent drawbacks to that apparatus for routine general use were that the recorder is expensive and bulky and it required the operator to manually read and record the endpoints. It is therefore the primary object of this invention to provide an electrochemical device for detecting micro-organisms which is inexpensive, compact and automatic.

Other objects and advantages of this invention will become apparent hereinafter in the specification and in the drawings.

SUMMARY OF THE INVENTION

A standard pH reference electrode and a platinum cathodic electrode are positioned in a container with a suitable nutrient medium for microbial growth plus the sample to be tested. The electrodes are connected to an analog-to-digital converter which includes an up/down binary counter. A clock provides pulses to the analog-to-digital converter, to a threshold counter, and to an 80 minute timer that inhibits the threshold counter for the first 80 minutes of operation. This time period allows the analog-to-digital converter to capture and track the electrode potential and also permits the electrode potential to stabilize after insertion of the sample into the nutrient medium. After the first 80 minutes the threshold counter counts the equivalent number of digital pulses from the clock that correspond to 10 millivolts (mv) of input potential change. When this time is reached, a signal from the threshold counter reverses the timer that was started when the nutrient medium was inoculated with the sample. The timer then times backwards until a count equivalent to an additonal 20 mv potential change is detected by the threshold counter. At this time the timer is stopped and displays a time interval equal to the length of time for the inoculum to begin the production of measurable amounts of $H_2$ after inoculation. This time interval is the measure of an endpoint.

BRIEF DESCRIPTION OF THE DRAWING

The sole FIGURE in this application is a block diagram of a preferred embodiment of the invention.

DETAILED DESCRIPTION OF THE INVENTION

Turning now to the embodiment of the invention selected for illustration in the drawing the number 11 designates a reference electrode and the number 12 designates a platinum electrode. These two electrodes are positioned in an electrically insulated container 13 with a suitable nutrient medium 14 for microbial growth plus the sample to be tested contained therein. The sample could be from a variety of sources where one is interested in detecting and enumerating the number of micro-organisms. For example, a sample of water for coliforms or a urine sample from a case of suspected urinary tract infection. The two electrodes are connected to a buffer amplifier 15 having an input resistance in excess of $10^6$ ohms. The buffer amplifier provides the required buffering to the electrodes and the necessary voltage gain to drive an analog-to-digital converter 16. Pulses are supplied to the analog-to-digital converter 16 by a clock oscillator 17 the frequency of which is selected to provide immunity to noise.

The analog-to-digital converter 16 includes a resistance 18 that is connected to the output of buffer amplifier 15 and to the input of an error amplifier 19. The output of error amplifier 19 is connected to an up/down counter 20 whose digital output is converted to an analog current by a digital-to-analog converter 21. The analog current from converter 21 is subtracted from the current applied to the input of error amplifier 19 through resistor 18. Up/down counter 20 includes a conventional up/down counter whose two inputs are controlled by two gates. The pulses from clock oscillator 17 are applied to both of these gates which are controlled by the analog signal at the output of error amplifier 19. The up/down counter 20 includes a binary decision circuit that selects which of the two gates is open to allow a pulse from the clock oscillator 17 to be counted. If the signal at the output of error amplifier 19 is positive the gate to the up count input to the up/down counter is opened allowing the pulse from the oscillator 17 to be counted up and if the output of error amplifier 19 is negative the gate to the down count input to the up/down counter is opened allowing the pulse to be counted down. The analog-to-digital converter 16 is calibrated such that a rise in potential of 1.2 mv at the two electrodes corresponds to a one up count. Hence a rise of 10 mv between the two electrodes corresponds to an eight up count by up/down counter 20. An up/-down counter 22 identical to updown counter 20 has its pulses supplied by clock oscillator 17 and is controlled by the output from error amplifier 19. However, it has been held in reset (zero count) for the initial 80 minutes.

The method used for the electronic sensing of an endpoint is governed by the manner in which the endpoints were formed by the test system mentioned above. It was apparent after examination of a number of strip chart recordings that the rate of departure from the baseline varied from test to test without any obvious correlation between inoculum size, test organism, media, or other factors. For example, in some cases the departure from the baseline was very gradual and required two hours to reach a level of 10 mv, in others 10 mv was reached in 30 minutes. Obviously the use of a preset level of 10 mv to indicate the endpoint would lead to erroneous results. Selection of the 10 mv level to indicate an endpoint was based upon previous studies which showed that false positive responses occured at levels below 10 mv. The endpoint problem was resolved when further examination of the strip chart recordings revealed that the response slopes for either the fast or slow case were fairly constant over a period of time. Taking advantage of the constant response rate for these curves, the following electronic system was designed to sense and record the endpoint.

A counter counts the equivalent number of digital pulses that correspond to 10 mv of input voltage change. When this is reached, a signal from the counter reverses the timer that was started when the medium nutrient was inoculated with the sample. After 20 mv more of input voltage change, the counter stops and displays a time equal to the length of time for the inoculum to begin the production of measurable amounts of $H_2$ after inoculation.

An up/down counter 23 acts as a timer and counts the clock pulses from clock oscillator 17 and displays this count on a display 24. Clock oscillator 17 has a frequency of 1 pulse per second, hence the count on display 24 reads in seconds. Up/down counter 23 is similar to the up/down counters 20 and 22 except that it does not have the binary decision circuits since it does not have an analog input. A logic circuit 25 connected between the output of up/down counter 23 and up/down counter 22 inhibits up/down counter 22 from counting until logic circuit 25 has a binary "1" applied to a all four of its inputs. Logic circuit 25 can be a four input nand circuit which has a binary "1" on its output until a binary "1" appears on all of its four inputs, at which time its output changes to a binary "0". Since clock oscillator 17 produces 1 pulse per second and it is required that up/down counter 22 be retained in its reset condition for 80 minutes it is necessary for up/down counter 23 to count 4800 pulses before up/down counter 22 begins to count. Logic circuit 25 performs this function.

After up/down counter 22 is started by logic circuit 25, each time there is positive potential change of 1.2 mv at the output of error amplifier 19 up/down counter 22 counts a pulse from clock oscillator 17 in the up direction. When there is a 10 mv positive potential change at the output of error amplifier 19, there is an up count of eight on counter 22. This corresponds to a binary "1" appearing on the $2^3$ output of counter 22. The $2^3$ output and the $2^4$ output of counter 22 is applied through a logic circuit 26 to the up/down counter 23 to cause it to start counting in the down direction as soon as a binary "1" appears on the $2^3$ output of counter 22. Counter 23 then counts down until binary "1's" appear on the $2^3$ and $2^4$ outputs of counter 22. This corresponds to a 30 mv potential change at the output of error amplifier 19. At this time the two binary "1's" applied to a logic circuit 27, which can be an "and" circuit, produce a binary "1" that is applied to clock oscillator 17 to stop its output and prevent any electrode input from changing the displayed time. The resulting number displayed on display 24 corresponds to the endpoint.

In the operation of this invention the inoculum is added to container 13 and the up/down counter 23 is reset to zero. After 80 minutes logic circuit 25 produces a signal which activates up/down counter 22 causing it to start its count. When there is a 10 mv change in the potential at the electrodes, up/down counter 22 will have produced eight pulses. Hence a binary "1" is applied to logic circuit 26 to reverse the count of counter 23 causing it to count down. When there is an additional 20 mv potential change at the electrodes there is a binary "1" at two of the outputs of up/down counter 22. These two binary "1's" are applied to logic circuit 27 causing the clock oscillator 17 to stop. At this time the count on display 24 represents the endpoint for the inoculum.

Examinations of a large number of strip chart records show that occasionally the baseline (voltage level after stabilization) exhibit a slow steady rise. Such a case can cause a 10 mv counter to reach its count earlier than it would with a flat baseline. To circumvent this problem, a circuit can be added that subtracts one digital count from the 10–30 mv counter often enough to prevent the observed nonsteady baseline from adversely affecting the correct detection of 10 mv and then 30 mv.

The advantages of this invention is that it provides a compact inexpensive electronic device which automatically determines the endpoint and displays it in hours and minutes in an electrochemical method for detecting micro-organisms based on a linear relationship between initial cell concentration and the time molecular hydrogen is detected.

What is claimed as new and desired to be secured by Letters Patent of the United States is:

1. Apparatus for measuring the elapsed time between inoculation and the initial increase in potential due to $H_2$ evolution in detecting micro-organisms comprising:
   a standard pH reference electrode and a platinum cathodic electrode positioned in a container with suitable nutrient medium for microbial growth plus a sample to be tested;
   an analog-to-digital converter including a first up/down counter connected to receive the potential between said reference and cathodic electrodes;
   a normally inactivated second up/down counter having its input connected to receive the input applied to said first up/down counter;
   a third up/down counter;
   a pulse source connected to said first, second, and third up/down counters;
   means responsive to a predetermined count of the pulses from said pulse source on said third up/down counter for activating said second up/down counter;
   means responsive to a first predetermined count of said second up/down counter which corresponds to a first predetermined level of potential change between said reference and cathodic electrodes for causing said third up/down counter to count down, and
   means responsive to a second predetermined count of said second up/down counter which corresponds to a second predetermined level of potential change between said reference and cathodic electrodes for causing said third up/down counter to stop counting whereby the count on said third up/down counter is indicative of the time for the inoculum to begin production of measurable amount of $H_2$ after inoculation.

2. Apparatus according to claim 1 wherein said predetermined count corresponds to 80 minutes.

3. Apparatus according to claim 1 wherein said first predetermined level of potential change is 10 mv and said second predetermined level of said potential change is 30 mv.

4. Apparatus according to claim 1 wherein said potential between said reference and cathodic electrodes is applied through a buffer amplifier to said analog-to-digital converter.

5. Apparatus according to claim 1 wherein said analog-to-digital converter includes an error amplifier that receives said potential between said reference and cathodic electrodes, said first up/down counter connected to the output of said error amplifier, a digital-to-analog converter connected to the output of said first up/down counter, and means for subtracting the output of said digital-to-analog converter from said potential between said reference and cathodic electrodes before it is applied to said error amplifier.

6. Apparatus for measuring the elapsed time between inoculation and the initial increase in potential due to $H_2$ evolution in detecting micro-organisms comprising:

a standard pH reference electrode and a platinum cathodic electrode positioned in a container with suitable nutrient medium for microbial growth plus a sample to be tested added at a selected time;

means for measuring the potential change between said reference electrode and said cathodic electrode;

means for measuring a predetermined first time interval beginning at said selected time;

means responsive to said means for measuring the potential change between said reference electrode and said cathodic electrode for adding to said predetermined time interval the time after said predetermined time interval it takes the potential change between said reference and cathodic electrodes to reach a first predetermined level to form a second time interval and for subtracting from said second time interval the time it takes the potential change between said reference and cathodic electrodes to go from said first predetermined level to a second predetermined level to form a third time interval whereby said third time interval is indicative of the elapsed time between said selected time and the initial increase in potential due to $H_2$ evolution.

7. Apparatus according to claim 6 wherein said means for measuring a predetermined first time interval is a source of clock pulses connected to be counted by a first up/down counter which has means attached to it that produces a signal representing the end of the first time interval when a predetermined number of pulses are counted.

8. Apparatus according to claim 7 wherein said means responsive to said means for measuring the potential change between said reference electrode and said cathodic electrode includes an analog-to-digital converter, a normally inactivated second up/down counter connected to said source of clock pulses, said analog-to-digital converter including a third up/down counter connected to said source of clock pulses and controlled by the said input to said third up/down counter, means receiving said signal representing the end of the first time interval for activating said second up/down counter, means connected to the output of second up/down counter for causing said first up/down counter to count down when said potential change reaches said first predetermined level and for causing said first up/down counter to stop when said potential reaches said second predetermined level.

9. Apparatus according to claim 7 wherein said first predetermined time interval is 80 minutes, said first predetermined level is 10 mv and said second predetermined level is 30 mv.

* * * * *